United States Patent
Nishimura et al.

(10) Patent No.: US 11,840,599 B2
(45) Date of Patent: Dec. 12, 2023

(54) THIOL-CONTAINING COMPOSITION FOR OPTICAL MATERIAL AND POLYMERIZABLE COMPOSITION FOR OPTICAL MATERIAL

(71) Applicant: MITSUI CHEMICALS, INC., Tokyo (JP)

(72) Inventors: Takeshi Nishimura, Yanagawa (JP); Masayuki Furuya, Arao (JP); Shigetoshi Kuma, Kurume (JP)

(73) Assignee: MITSUI CHEMICALS, INC., Tokyo (JP)

( * ) Notice: Subject to any disclaimer, the term of this patent is extended or adjusted under 35 U.S.C. 154(b) by 83 days.

(21) Appl. No.: 17/603,972

(22) PCT Filed: Apr. 24, 2020

(86) PCT No.: PCT/JP2020/017688
§ 371 (c)(1),
(2) Date: Oct. 15, 2021

(87) PCT Pub. No.: WO2020/218508
PCT Pub. Date: Oct. 29, 2020

(65) Prior Publication Data
US 2022/0204679 A1 Jun. 30, 2022

(30) Foreign Application Priority Data
Apr. 26, 2019 (JP) .................. 2019-085312

(51) Int. Cl.
*C08G 18/38* (2006.01)
*C07C 323/52* (2006.01)
(Continued)

(52) U.S. Cl.
CPC ........ *C08G 18/3876* (2013.01); *C07C 323/52* (2013.01); *C08G 18/244* (2013.01);
(Continued)

(58) Field of Classification Search
CPC .. C08G 18/3876; C08G 18/72; C08G 18/758; C08G 18/244; C08G 18/3891; C07C 323/52; G02B 1/041
See application file for complete search history.

(56) References Cited

U.S. PATENT DOCUMENTS

2009/0270583 A1 10/2009 Kuma et al.
2009/0281269 A1 11/2009 Sakata et al.
(Continued)

FOREIGN PATENT DOCUMENTS

JP 2011084479 A 4/2011
JP 2011126822 A 6/2011
(Continued)

*Primary Examiner* — Rabon A Sergent
(74) *Attorney, Agent, or Firm* — BUCHANAN INGERSOLL & ROONEY PC

(57) ABSTRACT

The thiol-containing composition for an optical material of the present invention includes a compound (A) represented by General Formula (a), and a compound (B) composed of at least one selected from a compound (b2-1) represented by General Formula (b2-1), a compound (b3-1) represented by General Formula (b3-1), a compound (b3-2) represented by General Formula (b3-2), and a compound (b4-2) represented by General Formula (b4-2), in which, in high-performance liquid chromatography measurement, the total peak area ratio of the compound included in the compound (B) is 0.1% to 60.0% with respect to the peak area 100 of the compound (A).

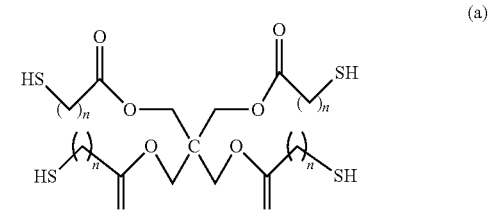

(a)

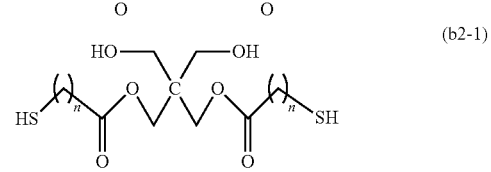

(b2-1)

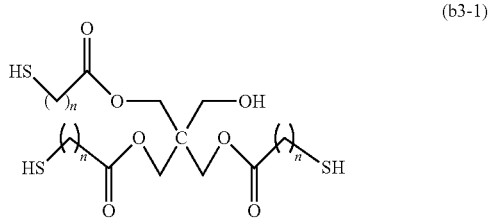

(b3-1)

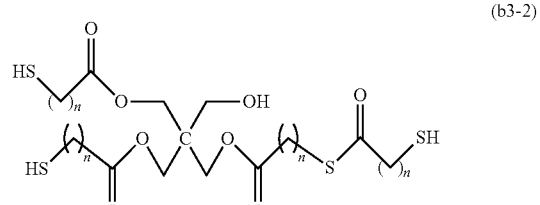

(b3-2)

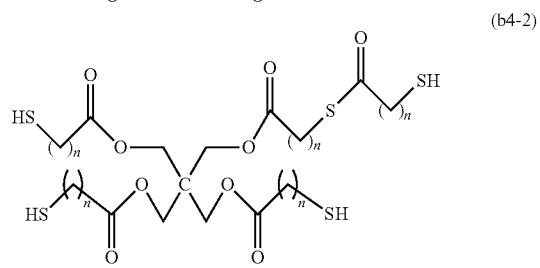

(b4-2)

18 Claims, 1 Drawing Sheet

(51) Int. Cl.
*C08G 18/72* (2006.01)
*C08G 18/24* (2006.01)
*C08G 18/75* (2006.01)
*G02B 1/04* (2006.01)

(52) U.S. Cl.
CPC ......... *C08G 18/3891* (2013.01); *C08G 18/72* (2013.01); *C08G 18/758* (2013.01); *G02B 1/041* (2013.01)

(56) References Cited

U.S. PATENT DOCUMENTS

2018/0186733 A1   7/2018  Kuma et al.
2019/0202969 A1   7/2019  Shim et al.

FOREIGN PATENT DOCUMENTS

| JP | 6691990 B1 | 5/2020 |
| KR | 101935031 B1 | 1/2019 |
| KR | 102062134 B1 | 1/2020 |
| WO | 2007052329 A1 | 5/2007 |
| WO | 2007122810 A1 | 11/2007 |
| WO | 2016208707 A1 | 12/2016 |

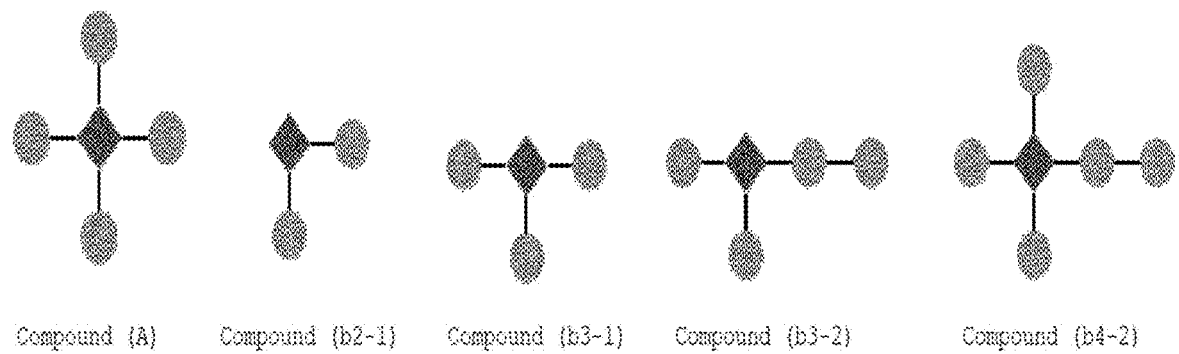

THIOL-CONTAINING COMPOSITION FOR OPTICAL MATERIAL AND POLYMERIZABLE COMPOSITION FOR OPTICAL MATERIAL

TECHNICAL FIELD

The present invention relates to a thiol-containing composition for an optical material and a polymerizable composition for an optical material.

BACKGROUND ART

Since ancient times, the main material used as an optical material has been glass; however, in recent years, a variety of plastics for optical materials have been developed and the use thereof as substitutes for glass is expanding. Also, as materials for spectacle lenses and the like, plastic materials such as acrylic resins, aliphatic carbonate resins, polycarbonates, and polythiourethanes are mainly used due to having excellent optical characteristics, being lightweight and unbreakable, and also having excellent moldability. Among the above, typical examples having high refractive indices include polythiourethane resins obtained from polymerizable compositions including isocyanate compounds and thiol compounds.

Among polythiourethane resins, polythiourethane resins obtained by polymerization of pentaerythritol mercaptocarboxylic acid esters and polyiso(thio)cyanate compounds are one of the most suitable resins for plastic lenses due to the high refractive index thereof. However, plastic lenses using pentaerythritol mercaptocarboxylic acid esters may have problems such as clouding.

Patent Document 1 discloses a method for producing pentaerythritol mercaptocarboxylic acid esters by reacting pentaerythritol, which has an alkali metal or alkaline earth metal content of 1.0% by weight or less, with a mercaptocarboxylic acid. The above document describes that lenses with excellent transparency were obtained from the obtained pentaerythritol mercaptocarboxylic acid ester and a polyiso(thio)cyanate compound.

Patent Document 2 discloses a method for producing pentaerythritol mercaptocarboxylic acid esters by reacting a mercaptocarboxylic acid including a predetermined amount of a bimolecularly condensed thioester compound with pentaerythritol. The above document describes that the composition including the obtained pentaerythritol mercaptocarboxylic acid ester and a polyiso(thio)cyanate compound has low viscosity and, furthermore, that the lenses composed of the composition have excellent transparency.

Patent Documents 3 and 4 disclose a method for producing mercaptocarboxylic acid polyhydric alcohol esters by reacting mercaptocarboxylic acid with a polyhydric alcohol under predetermined conditions. The above document describes the production of the desired tetraesterified products as well as diesterified products, triesterified products, and the like. These documents do not describe the use of the obtained mercaptocarboxylic acid polyhydric alcohol ester as a raw material for an optical material.

Patent Document 5 discloses a polythiol composition including pentaerythritol tetrakismercaptopropionate or pentaerythritol tetrakismercaptoacetate, a polythiol compound provided with a predetermined structure, and other oligomers other than the compound.

RELATED DOCUMENT

Patent Document

[Patent Document 1] International Publication No. 2007/052329
[Patent Document 2] International Publication No. 2007/122810
[Patent Document 3] Japanese Unexamined patent publication NO. 2011-126822
[Patent Document 4] Japanese Unexamined patent publication NO. 2011-084479
[Patent Document 5] Korean Registered Patent No. 10-1935031

SUMMARY OF THE INVENTION

Technical Problem

According to the techniques described in the above documents, although it is possible to obtain lenses with excellent transparency and the like, there is room for improvement in other optical properties, mechanical properties such as strength, dyeability, and the like and there is room for improvement in the handleability of the polymerizable composition and the like.

Solution to Problem

That is, it is possible to illustrate the present invention as follows.

[1] A thiol-containing composition for an optical material including a compound (A) represented by General Formula (a)

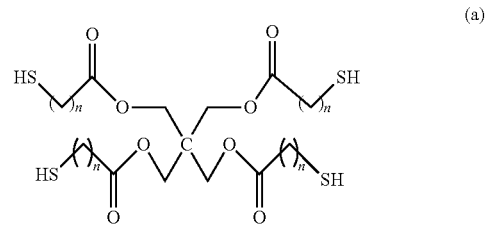

wherein, in General Formula (a), n is an integer of 1 to 3, and a plurality of present n's may be the same or different, and a compound (B) composed of one or two or more compounds selected from the group consisting of a compound (b2-1) represented by General Formula (b2-1), a compound (b3-1) represented by General Formula (b3-1), a compound (b3-2) represented by General Formula (b3-2), and a compound (b4-2) represented by General Formula (b4-2), in which in high-performance liquid chromatography measurement, a total peak area ratio of the compound included in the compound (B) is 0.1% to 60.0% with respect to a peak area 100 of the compound (A),

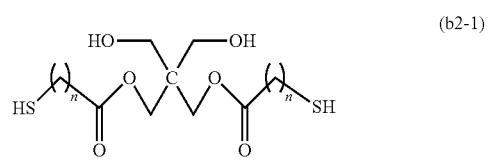

-continued

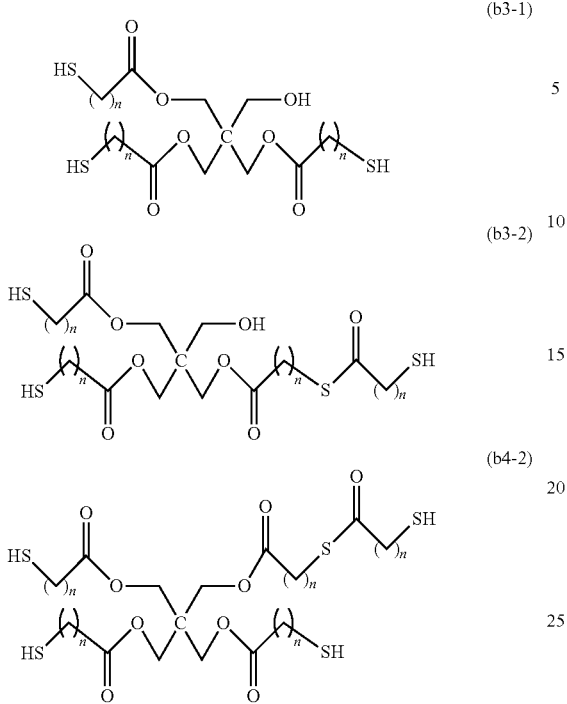

(b3-1)

(b3-2)

(b4-2)

wherein, in General Formula (b2-1), General Formula (b3-1), General Formula (b3-2), and General Formula (b4-2), n is an integer of 1 to 3, and in each General Formula, a plurality of present n's may be the same or different.

[2] The thiol-containing composition for an optical material according to [1], in which, in the high-performance liquid chromatography measurement, the total peak area ratio of the compound included in the compound (B) is 0.1% to 40.0% with respect to the peak area 100 of the compound (A).

[3] The thiol-containing composition for an optical material according to [1] or [2], including the compound (A) represented by General Formula (a)

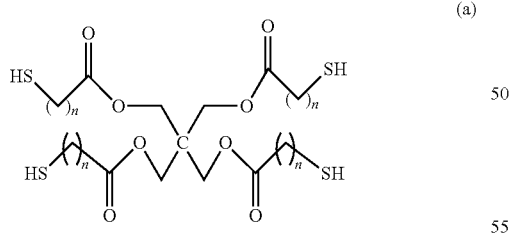

(a)

wherein, in General Formula (a), n is an integer of 1 to 3, and a plurality of present n's may be the same or different, and
a compound (B) composed of the compound (b2-1) represented by General Formula (b2-1), the compound (b3-1) represented by General Formula (b3-1), the compound (b3-2) represented by General Formula (b3-2), and the compound (b4-2) represented by General Formula (b4-2),
in which in high-performance liquid chromatography measurement, a total peak area ratio of the compounds included in the compound (B) is 0.1% to 40.0%, and a total peak area ratio of the compound (b3-2) and the compound (b4-2) is 20.0% or less, with respect to the peak area 100 of the compound (A),

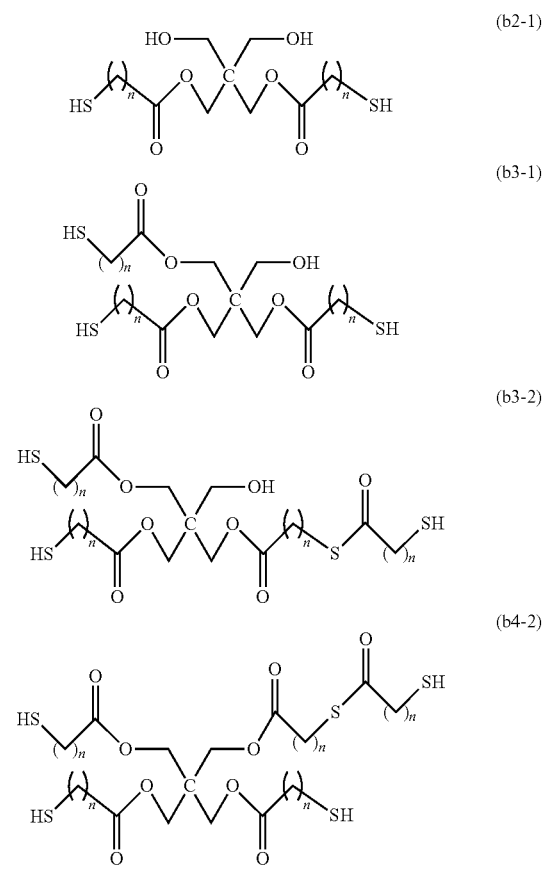

(b2-1)

(b3-1)

(b3-2)

(b4-2)

wherein, in General Formula (b2-1), General Formula (b3-1), General Formula (b3-2), and General Formula (b4-2), n is an integer of 1 to 3, and in each General Formula, a plurality of present n's may be the same or different.

[4] The thiol-containing composition for an optical material according to [1] or [2], including the compound (A) represented by General Formula (a)

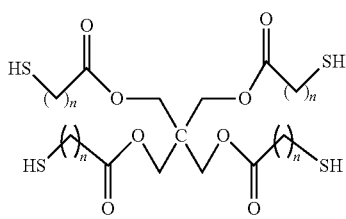

(a)

wherein, in General Formula (a), n is an integer of 1 to 3, and a plurality of present n's may be the same or different, and
the compound (B) composed of one or two or more compounds selected from the group consisting of the compound (b2-1) represented by General Formula (b2-1), the compound (b3-1) represented by General Formula (b3-1), the compound (b3-2) represented by General Formula (b3-2), and the compound (b4-2) represented by General Formula (b4-2), in which, in high-performance liquid chromatography measurement, a peak area ratio of the compound (b2-1) is 0.0%, the total peak area ratio of the compound included in the compound (B) is 0.1% to 40.0%, and a total peak area ratio of the compound (b3-2) and the compound (b4-2) is 20.0% or less, with respect to the peak area 100 of the compound (A),

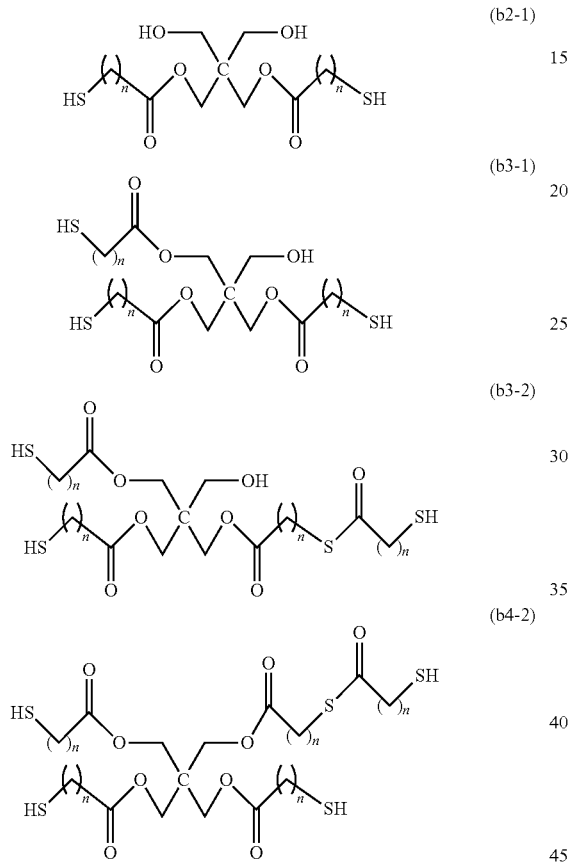

wherein, in General Formula (b2-1), General Formula (b3-1), General Formula (b3-2), and General Formula (b4-2), n is an integer of 1 to 3, and in each General Formula, a plurality of present n's may be the same or different.

[5] The thiol-containing composition for an optical material according to any one of [1] to [4], in which, in high-performance liquid chromatography measurement, the total peak area ratio of the compound included in the compound (B) is 10.0% to 40.0% with respect to the peak area 100 of the compound (A).

[6] The thiol-containing composition for an optical material according to any one of [1], [2], or [5], in which, in high-performance liquid chromatography measurement, a total peak area ratio of the compound (b3-2) and the compound (b4-2) is 20.0% or less with respect to the peak area 100 of the compound (A).

[7] The thiol-containing composition for an optical material according to any one of [1] to [6], in which, in high-performance liquid chromatography measurement, a peak area ratio of the compound (b2-1) is 5.0% or less with respect to the peak area 100 of the compound (A).

[8] The thiol-containing composition for an optical material according to any one of [1] to [7], in which, in high-performance liquid chromatography measurement, a peak area ratio of the compound (b3-2) is 5.0% or less with respect to the peak area 100 of the compound (A).

[9] The thiol-containing composition for an optical material according to any one of [1] to [8], in which, in high-performance liquid chromatography measurement, a peak area ratio of the compound (b4-2) is 20.0% or less with respect to the peak area 100 of the compound (A).

[10] A thiol-containing composition for an optical material including a compound (A) represented by General Formula (a)

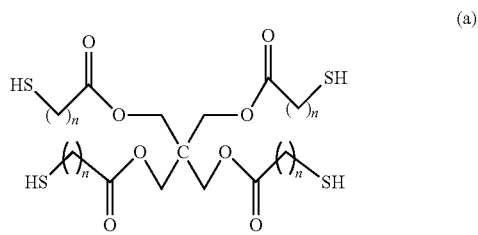

wherein, in General Formula (a), n is an integer of 1 to 3, and a plurality of present n's may be the same or different, and
a compound (b2-1) represented by General Formula (b2-1)

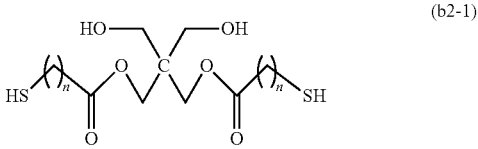

wherein, in General Formula (b2-1), n is an integer of 1 to 3.

[11] The thiol-containing composition for an optical material according to [10], in which, in high-performance liquid chromatography measurement, a peak area ratio of the compound (b2-1) is 5% or less with respect to a peak area 100 of the compound (A).

[12] A thiol-containing composition for an optical material, including a compound (A) represented by General Formula (a)

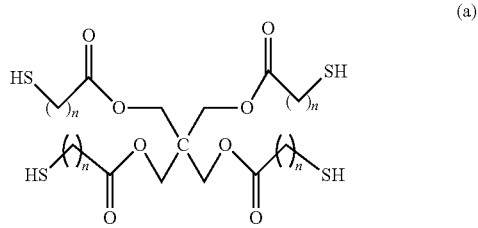

wherein, in General Formula (a), n is an integer of 1 to 3, and a plurality of present n's may be the same or different; and a compound (b3-2) represented by General Formula (b3-2)

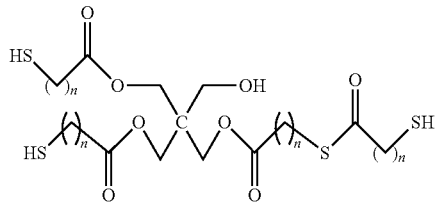

(b3-2)

wherein, in General Formula (b3-2), n is an integer of 1 to 3, and a plurality of present n's may be the same or different.

[13] The thiol-containing composition for an optical material according to [12], in which, in high-performance liquid chromatography measurement, a peak area ratio of the compound (b3-2) is 5% or less with respect to a peak area 100 of the compound (A).

[14] A thiol-containing composition for an optical material including a compound (A) represented by General Formula (a)

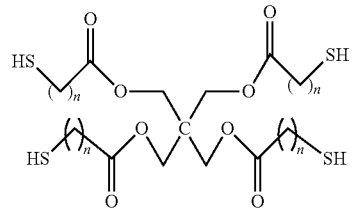

(a)

wherein, in General Formula (a), n is an integer of 1 to 3, and a plurality of present n's may be the same or different; and
a compound (b4-2) represented by General Formula (b4-2)

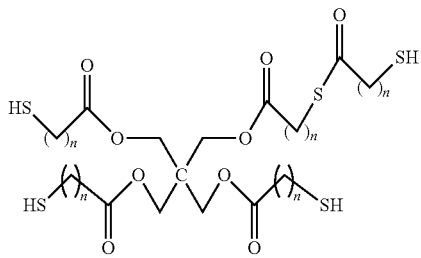

(b4-2)

wherein, in General Formula (b4-2), n is an integer of 1 to 3, and a plurality of present n's may be the same or different.

[15] The thiol-containing composition for an optical material according to [14], in which, in high-performance liquid chromatography measurement, a peak area ratio of the compound (b4-2) is 20% or less with respect to a peak area 100 of the compound (A).

[16] A thiol-containing composition for an optical material including a compound (A) represented by General Formula (a)

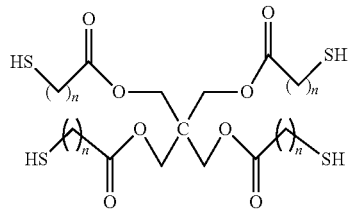

(a)

wherein, in General Formula (a), n is an integer of 1 to 3, and a plurality of present n's may be the same or different;
a compound (b2-1) represented by General Formula (b2-1); and
a compound (b3-2) represented by General Formula (b3-2) and/or a compound (b4-2) represented by General Formula (b4-2)

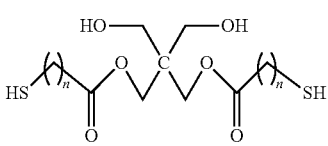

(b2-1)

wherein, in General Formula (b2-1), n is an integer of 1 to 3,

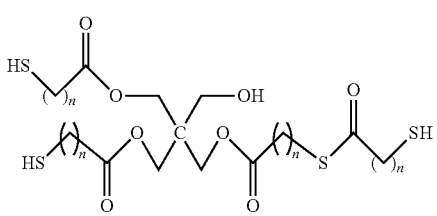

(b3-2)

wherein, in General Formula (b3-2), n is an integer of 1 to 3, and a plurality of present n's may be the same or different,

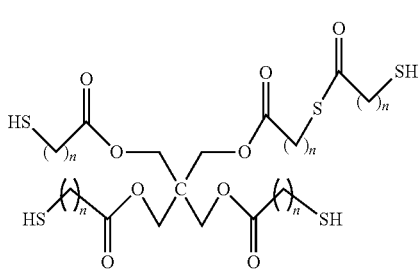

(b4-2)

wherein, in General Formula (b4-2), n is an integer of 1 to 3, and a plurality of present n's may be the same or different.

[17] The thiol-containing composition for an optical material according to [16], in which, in high-performance liquid chromatography measurement, a total peak area ratio of the compound (b2-1) and compound (b3-2) and/or compound (b4-2) is 25.0% or less with respect to a peak area 100 of the compound (A).

[18] A thiol-containing composition for an optical material including a compound (A) represented by General Formula (a)

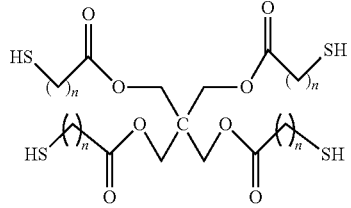
(a)

wherein, in General Formula (a), n is an integer of 1 to 3, and a plurality of present n's may be the same or different;

a compound (b3-2) represented by General Formula (b3-2); and a compound (b4-2) represented by General Formula (b4-2)

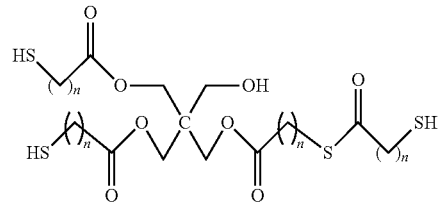
(b3-2)

wherein, in General Formula (b3-2), n is an integer of 1 to 3, and a plurality of present n's may be the same or different,

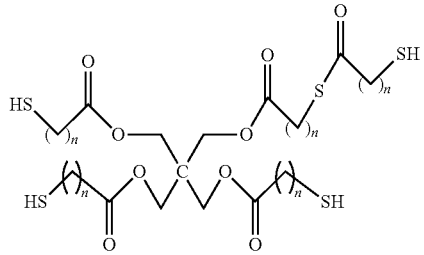
(b4-2)

wherein, in General Formula (b4-2), n is an integer of 1 to 3, and a plurality of present n's may be the same or different.

[19] The thiol-containing composition for an optical material according to [18], in which, in high-performance liquid chromatography measurement, a total peak area ratio of the compound (b3-2) and the compound (b4-2) is 20.0% or less with respect to a peak area 100 of the compound (A).

[20] A thiol-containing composition for an optical material including a compound (A) represented by General Formula (a)

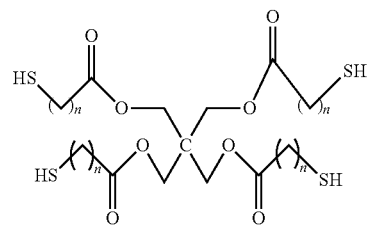
(a)

wherein, in General Formula (a), n is an integer of 1 to 3, and a plurality of present n's may be the same or different;

a compound (b3-1) represented by General Formula (b3-1);

a compound (b3-2) represented by General Formula (b3-2); and a compound (b4-2) represented by General Formula (b4-2)

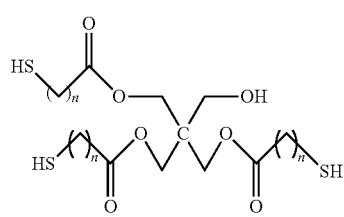
(b3-1)

wherein, in General Formula (b3-1), n is an integer of 1 to 3,

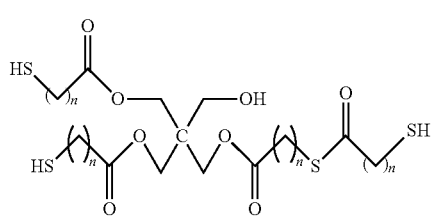
(b3-2)

wherein, in General Formula (b3-2), n is an integer of 1 to 3, and a plurality of present n's may be the same or different,

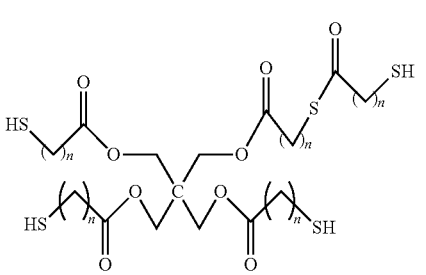
(b4-2)

wherein, in General Formula (b4-2), n is an integer of 1 to 3, and a plurality of present n's may be the same or different.

[21] The thiol-containing composition for an optical material according to [20], in which, in high-performance liquid chromatography measurement, a total peak area ratio of the compound (b3-1), the compound (b3-2), and the compound (b4-2) is 40.0% or less with respect to a peak area 100 of the compound (A).

[22] The thiol-containing composition for an optical material according to any one of [1] to [21], in which the compound (A) is pentaerythritol tetrakismercaptopropionate, and n in the General Formula in the compound (B) is 2. [23] The thiol-containing composition for an optical material according to any one of [1] to [21], in which the compound (A) is pentaerythritol tetrakismercaptoacetate, and n in the General Formula in the compound (B) is 1. [24] A polymerizable composition for an optical material including the thiol-containing composition for an optical material according to any one of [1] to [23], and a polyiso(thio)cyanate compound.

[25] The polymerizable composition for an optical material according to [24], in which the polyiso(thio)cyanate compound includes at least one selected from 2,5-bis(isocyanatomethyl)bicyclo-[2.2.1]-heptane, 2,6-bis(isocyanatomethyl)bicyclo-[2.2.1]-heptane, xylylene diisocyanate, bis(isocyanatocyclohexyl)methane, bis(isocyanatomethyl)cyclohexane, isophorone diisocyanate, hexamethylene diisocyanate, pentamethylene diisocyanate, tolylene diisocyanate, diphenylmethane diisocyanate, and phenylene diisocyanate.

[26] A molded product formed by curing the polymerizable composition for an optical material according to [24] or [25].

[27] An optical material composed of the molded product according to [26].

[28] A plastic lens composed of the molded product according to [26].

[29] The plastic lens according to [28], in which a thioester group molar number is 0.0003 mmol/g to 0.146 mmol/g.

BRIEF DESCRIPTION OF DRAWING

The drawing schematically shows the compound (A), the compound (b2-1), the compound (b3-1), the compound (b3-2), and the compound (b4-2).

ADVANTAGEOUS EFFECTS OF INVENTION

Regarding the thiol-containing composition for an optical material of the present invention, a polymerizable composition including the thiol-containing composition and another polymerizable compound has excellent handleability and, furthermore, an optical material obtained from the polymerizable composition has excellent optical properties such as refractive index, Abbe number, cloudiness, distortion, and striae, mechanical properties such as strength, dyeability, and the like.

That is, by using the thiol-containing composition for an optical material of the present invention, the balance of these characteristics is excellent.

DESCRIPTION OF EMBODIMENTS

A description will be given of the thiol-containing composition for an optical material of the present invention based on embodiments. In the present embodiment, "1 to 5" denotes "equal to or more than 1" and "equal to or less than 5" unless otherwise noted.

[Thiol-Containing Composition For Optical Material]

The thiol-containing composition for an optical material of the present embodiment includes a compound (A) represented by General Formula (a), and a compound (B) composed of one or two or more compounds selected from the group consisting of a compound (b2-1) represented by General Formula (b2-1), a compound (b3-1) represented by General Formula (b3-1), a compound (b3-2) represented by General Formula (b3-2), and a compound (b4-2) represented by General Formula (b4-2).

(Compound (A))

In the present embodiment, the compound (A) is represented by General Formula (a).

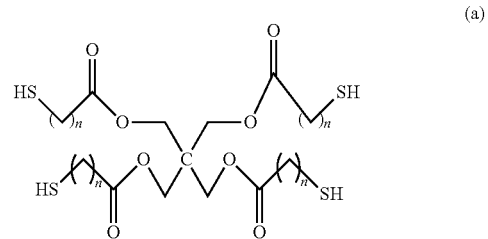

(a)

In General Formula (a), n is an integer of 1 to 3. A plurality of present n's may be the same or may be different and are preferably the same. n is preferably 1 or 2, and more preferably 2.

The compound (A) includes at least one selected from the compounds represented by General Formula (a).

Examples of the compound (A) include pentaerythritol tetrakismercaptoacetate, pentaerythritol tetrakismercaptopropionate, pentaerythritol tetrakismercaptobutyrate, and the like, and pentaerythritol tetrakismercaptoacetate and pentaerythritol tetrakismercaptopropionate are preferable. It is possible for the compound (A) to include at least one selected from these compounds.

(Compound (B))

The compound (B) is composed of one or two or more compounds selected from the group consisting of the compound (b2-1) represented by General Formula (b2-1), the compound (b3-1) represented by General Formula (b3-1), the compound (b3-2) represented by General Formula (b3-2), and the compound (b4-2) represented by General Formula (b4-2).

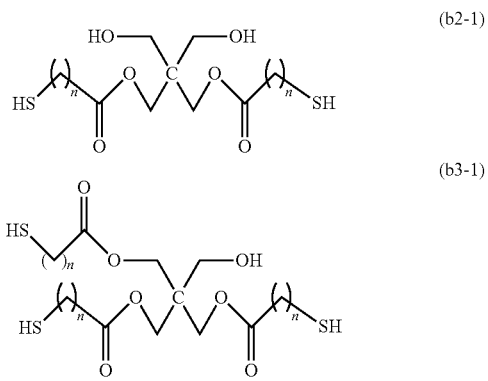

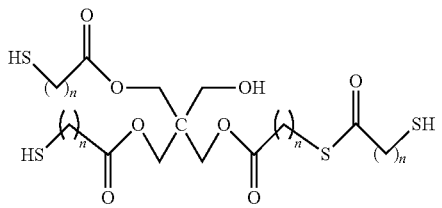
(b3-2)

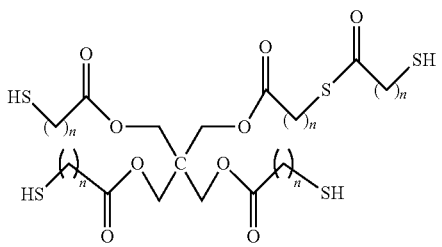
(b4-2)

In General Formula (b2-1), General Formula (b3-1), General Formula (b3-2), and General Formula (b4-2), n is an integer of 1 to 3. A plurality of present n's may be the same or may be different and are preferably the same. n is preferably 1 or 2, and more preferably 2.

It is possible for these compounds to include at least one selected from the compounds represented by the respective General Formulae.

The compound (A), the compound (b2-1), the compound (b3-1), the compound (b3-2), and the compound (b4-2) represented by the above General Formulae are schematically represented in the drawing. The diamond-shaped portion is the structure of a portion of a pentaerythritol-derived group excluding the hydroxyl group and the circle portions are a mercaptocarboxylic acid-derived group after an esterification reaction between pentaerythritol and mercaptocarboxylic acid or a mercaptocarboxylic acid-derived group after a thioesterification reaction between the group and mercaptocarboxylic acid.

In the present embodiment, the compound (B) is composed of one or two or more compounds selected from the group consisting of the compound (b2-1), the compound (b3-1), the compound (b3-2), and the compound (b4-2).

From the viewpoint of the effect of the present invention, in high-performance liquid chromatography measurement performed under the conditions described below, the lower limit value of the total peak area ratio of the compounds included in the compound (B) is 0.1% or more, preferably 10.0% or more, and more preferably 15.0% or more, with respect to the peak area 100 of the compound (A). The upper limit value is 60.0% or less, preferably 50.0% or less, more preferably 40.0% or less, even more preferably 30.0% or less, and particularly preferably 20.0% or less. In the present embodiment, the total peak area of the compound included in the compound (B) is obtained by totaling the peak areas of each of the compound (b2-1), the compound (b3-1), the compound (b3-2), and the compound (b4-2) measured by high-performance liquid chromatography.

(Conditions for High-Performance Liquid Chromatography Measurement)
HPLC model: SPD-10A produced by Shimadzu Corporation
Detector: RI detector
Column: YMC column ODS-A-312 (150 mm×6 mm. I.D.) 5 µm
Temperature condition: 40° C.
Mobile phase: Water/acetonitrile (35 vol/65 vol) aqueous solution
Flow rate: 1.0 ml/min
Analysis sample preparation: Mix and dissolve 3 g of sample with 3 g of acetonitrile
Injection volume: 1 µL In a case where the compound (B) is composed of one or two or more compounds selected from the group consisting of the compound (b3-1), the compound (b3-2), and the compound (b4-2), from the viewpoint of the effect of the present invention, in high-performance liquid chromatography measurement performed under the conditions described above, the lower limit value of the total peak area ratio of the compounds included in the compound (B) is 0.1% or more, preferably 10.0% or more, and even more preferably 15.0% or more, with respect to the peak area 100 of the compound (A). The upper limit value is 60.0% or less, preferably 50.0% or less, more preferably 40.0% or less, even more preferably 30.0% or less, and particularly preferably 20.0% or less. Furthermore, the total peak area ratio of the compound (b3-2) and the compound (b4-2) is 20.0% or less, preferably 17.0% or less, and more preferably 15.0% or less.

The compound (B) in the present embodiment is one or two or more compounds selected from the group consisting of the compound (b2-1), the compound (b3-1), the compound (b3-2), and the compound (b4-2) In high-performance liquid chromatography measurement performed under the conditions described above, the peak area ratio of each compound included in the compound (B) with respect to the peak area 100 of the compound (A) is as follows.

Compound (B2-1): Preferably 5.0% or less, more preferably 3.0% or less, and particularly preferably 2.0% or less Compound (b3-1): Preferably 35.0% or less, more preferably 32.0% or less, and particularly preferably 30.0% or less Compound (b3-2): Preferably 5.0% or less, more preferably 3.0% or less, and particularly preferably 2.0% or less Compound (b4-2): Preferably 20.0% or less, more preferably 18.0% or less, and particularly preferably 17.0% or less Specifically, the compound (B) in the present embodiment preferably includes a compound or a group of compounds of any of Example 1 to Example 7 below.

Example 1: Compound (b2-1)
Example 2: Compound (b3-2)
Example 3: Compound (b4-2)
Example 4: Compound (b2-1), compound (b3-2) and/or compound (b4-2)
Example 5: Compound (b3-2) and compound (b4-2)
Example 6: Compound (b3-1), compound (b3-2), and compound (b4-2)
Example 7: Compound (b2-1), compound (b3-1), compound (b3-2), and compound (b4-2)

A detailed description will be given below of Example 1 to Example 7 described above.

Example 1

A description will be given of Example 1 described above.
The compound (B) in Example 1 includes the compound (b2-1).
In the present embodiment, from the viewpoint of balancing the handleability of the obtained polymerizable composition and the refractive index of the optical material, in high-performance liquid chromatography measurement performed under the conditions described above, the peak area ratio of the compound (b2-1) is preferably 5.0% or less, more preferably 3.0% or less, and particularly preferably 2.0% or less, with respect to the peak area 100 of the compound (A).

Example 2

A description will be given of Example 2 described above.

The compound (B) in Example 2 includes the compound (b3-2).

In the present embodiment, from the viewpoint of balancing the handleability of the obtained polymerizable composition and the striae of the optical material, in high-performance liquid chromatography measurement performed under the conditions described above, the peak area ratio of the compound (b3-2) is preferably 5.0% or less, more preferably 3.0% or less, and particularly preferably 2.0% or less, with respect to the peak area 100 of the compound (A).

Example 3

A description will be given of Example 3 described above.

The compound (B) in Example 3 includes the compound (b4-2).

In the present embodiment, from the viewpoint of balancing the handleability of the obtained polymerizable composition and the refractive index and striae of the optical material, in high-performance liquid chromatography measurement performed under the conditions described above, the peak area ratio of the compound (b4-2) is preferably 20.0% or less, more preferably 18.0% or less, and particularly preferably 17.0% or less, with respect to the peak area 100 of the compound (A).

Example 4

A description will be given of Example 4 described above.

The compound (B) in Example 4 includes the compound (b2-1) and the compound (b3-2) and/or the compound (b4-2).

In the present embodiment, from the viewpoint of balancing the handleability of the polymerizable composition and the dyeability, refractive index, and striae of the optical material, in high-performance liquid chromatography measurement performed under the conditions described above, the total peak area ratio of the compounds (b2-1) and (b3-2) and/or (b4-2) is preferably 25.0% or less, more preferably 20.0% or less, and particularly preferably 18.0% or less, with respect to the peak area 100 of the compound (A).

Example 5

A description will be given of Example 5 described above.

The compound (B) in Example 5 includes the compound (b3-2) and the compound (b4-2).

In the present embodiment, from the viewpoint of balancing the handleability of the obtained polymerizable composition and the refractive index of the optical material, in high-performance liquid chromatography measurement performed under the conditions described above, the total peak area ratio of the compound (b3-2) and the compound (b4-2) is preferably 20.0% or less, more preferably 17.0% or less, and particularly preferably 15.0% or less, with respect to the peak area 100 of the compound (A).

Example 6

A description will be given of Example 6 described above.

The compound (B) in Example 6 includes the compound (b3-1), the compound (b3-2), and the compound (b4-2).

In the present embodiment, from the viewpoint of the balance between the handleability of the obtained polymerizable composition and the refractive index and dyeability of the optical material, in high-performance liquid chromatography measurement performed under the conditions described above, the total peak area ratio of the compound (b3-1), the compound (b3-2), and the compound (b4-2) is preferably 60.0% or less, more preferably 50.0% or less, even more preferably 40.0% or less, particularly preferably 30.0% or less, and more particularly preferably 20.0% or less, with respect to the peak area 100 of the compound (A).

Example 7

A description will be given of Example 7 described above.

The compound (B) in Example 7 includes the compound (b2-1), the compound (b3-1), the compound (b3-2), and the compound (b4-2).

In the present embodiment, from the viewpoint of the effect of the present invention, in high-performance liquid chromatography measurement performed under the conditions described above, the lower limit value of the total peak area ratio of the compound (b2-1), the compound (b3-1), the compound (b3-2), and the compound (b4-2) is preferably 0.1% or more, more preferably 10.0% or more, and particularly preferably 15.0% or more, with respect to the peak area 100 of the compound (A). The upper limit value is preferably 60.0% or less, more preferably 50.0% or less, even more preferably 40.0% or less, particularly preferably 30.0% or less, and more particularly preferably 20.0% or less. Furthermore, in the above combination, the total peak area ratio of the compound (b3-2) and the compound (b4-2) is preferably 20.0% or less, more preferably 17.0% or less, and particularly preferably 15% or less.

The thiol-containing composition for an optical material of the present embodiment may include compounds as below in a range in which the effect of the present invention is not impaired.

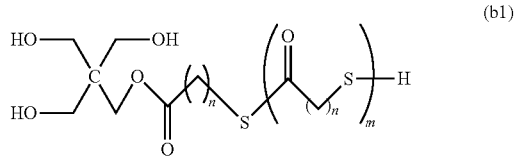

(b1)

In General Formula (b1), n is an integer of 1 to 3, preferably 1 or 2, and more preferably 2. The plurality of present n's may be 5 the same numbers or different numbers and are preferably the same. m is an integer of 0 to 3.

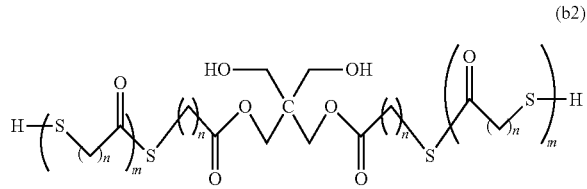

(b2)

In General Formula (b2), n is an integer of 1 to 3, preferably 1 or 2, and more preferably 2. m is an integer of 0 to 3. The plurality of present m and n may be the same numbers or different numbers, but n is preferably the same. No two m's are 0 at the same time.

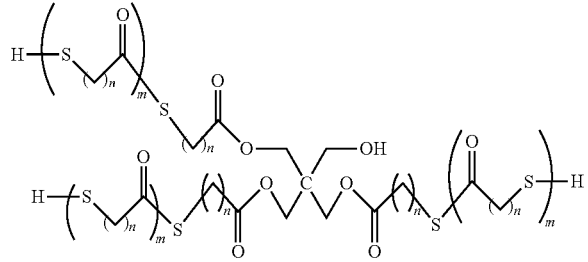

(b3)

In General Formula (b3), n is an integer of 1 to 3, preferably 1 or 2, and more preferably 2. m is an integer of 0 to 3. The plurality of present m and n may be the same numbers or different numbers, but n is preferably the same. No two m's are 0, no one m is 1, and all m's are not 0 at the same time.

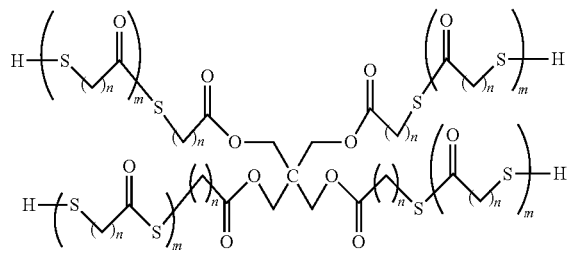

(b4)

In General Formula (b4), n is an integer of 1 to 3, preferably 1 or 2, and more preferably 2. m is an integer of 0 to 3. The plurality of present m and n may be the same numbers or different numbers, but n is preferably the same. No three selected from m is 0, no one is 1, and all of m are not 0 at the same time.

Patent Document 5 describes a polythiol compound including the compound (A) and the compound (b3-1) in the present embodiment and describes further including other "oligomers" excluding these compounds.

In general, an oligomer is a polymer with a number (degree of polymerization) of repeating structural units from 2 to 20 approximately. This definition is described in the Dictionary of Science and Chemistry and the like, for example. In other words, an oligomer is defined as a polymer in which the structural units are repeated.

Therefore, in the composition of the present embodiment, among the compounds included in the compound (B), the compound (b3-2) and the compound (b4-2) are polymers in which the structural units are repeated and these compounds correspond to oligomers according to the above definition of oligomer.

Furthermore, in the compounds (b1) to (b4), compounds where m is 2 or more also correspond to oligomers according to the above definition of oligomer.

On the other hand, the compound (b2-1) does not correspond to an oligomer according to the above definition of oligomer.

In the present embodiment, from the viewpoint of the effect of the present invention, the compound (A) and the compound (B) are preferably the combinations of (1) or (2) below, and more preferably the combination of (1).

(1) Compound (A) is pentaerythritol tetrakismercaptopropionate and, in at least one compound selected from the compound (b2-1), the compound (b3-1), the compound (b3-2), and the compound (b4-2) included in the compound (B), n is 2.

(2) Compound (A) is pentaerythritol tetrakismercaptoacetate and, in at least one compound selected from the compound (b2-1), the compound (b3-1), the compound (b3-2), and the compound (b4-2) included in the compound (B), n is 1.

The thiol-containing composition for an optical material of the present embodiment includes the compound (B) together with the compound (A) and the overall yield is high.

[Method for Producing Thiol-Containing Composition for Optical Material]

It is possible to obtain the thiol-containing composition for an optical material in the present embodiment, for example, by reacting pentaerythritol with a mercaptocarboxylic acid.

Examples of mercaptocarboxylic acids include thioglycolic acid, 3-mercaptopropionic acid, 4-mercaptobutanoic acid, and the like. In addition, these can be reacted alone or in combination of two or more with pentaerythritol. The quality of the mercaptocarboxylic acid is not particularly limited and it is possible to use ordinary industrial products.

As an esterification catalyst normally used to react pentaerythritol with mercaptocarboxylic acid, for example, mineral acids such as sulfuric acid, hydrochloric acid, phosphoric acid, and alumina, organic acids such as p-toluenesulfonic acid, benzenesulfonic acid, methanesulfonic acid, and trichloroacetic acid, and acid catalysts represented by organometallic compounds such as dibutyl tin dioxide are preferably used.

It is possible for the total peak area ratio of at least one compound selected from the compound (b2-1), the compound (b3-1), the compound (b3-2), and the compound (b4-2) included in the compound (B) with respect to the compound (A) in high-performance liquid chromatography measurement to be adjusted according to the molar ratio of mercaptocarboxylic acid with respect to pentaerythritol or reaction conditions (concentration of the compound in a solvent, reaction temperature, dehydration rate, and the like) described below.

The molar ratio of mercaptocarboxylic acid with respect to pentaerythritol may be 3.2 or more, for example, 3.2 to 4.5, preferably 3.2 to 4.1, even more preferably 3.2 or more and less than 4.0, and particularly preferably 3.5 or more and less than 4.0. Even if the molar ratio is outside the above range, it is possible to obtain the thiol-containing composition for an optical material of the present invention by adjusting the reaction conditions (concentration of the compound in a solvent, reaction temperature, dehydration rate, and the like), and the like described below.

In the present embodiment, the production of the thiol-containing composition for an optical material may be performed in a solvent. The use of an azeotropic agent is not an essential condition and, for example, it is possible to carry out the reaction in a solvent using an azeotropic agent under heating and refluxing while continuously removing the water by-product from the system. In the present embodiment, it is preferable to use an azeotropic agent as the solvent. Examples of typically used solvents and azeotropic agents include benzene, toluene, xylene, nitrobenzene, chlorobenzene, dichlorobenzene, anisole, diphenyl ether, methylene chloride, chloroform, dichloroethane, and the like. These may be used in a mixture of two or more or used in a mixture with other solvents.

In the present embodiment, it is possible to control a step of continuously removing the water by-product from the system according to the ratio (%) of the amount of water extracted with respect to the theoretical amount of produced water shown in the following equation.

Equation: Ratio (%) of the amount of water extracted from the system with respect to the theoretical amount of produced water=[(Amount of water actually extracted−Amount of water present before the reaction)/theoretical amount of produced water]×100

The theoretical amount of produced water as indicated in the present invention is the amount of water calculated on the assumption that 4 moles of mercaptocarboxylic acid react with respect to 1 mole of pentaerythritol to obtain the compound (A) at 100% yield, regardless of the molar ratio of mercaptocarboxylic acid with respect to pentaerythritol.

The amount of water extracted from the system means the amount of water produced in the reaction and excludes water present before the reaction, for example, water included in raw materials, catalysts, solvents, and the like.

The ratio of the amount of water extracted from the system with respect to the theoretical amount of produced water (dehydration rate) (%) is 85% to 99%, preferably 86% to 95%, and even more preferably 86% to 93%. Even when the dehydration rate is outside the above range, it is possible to obtain the thiol-containing composition for an optical material of the present invention by adjusting the reaction conditions (concentration of the compound in a solvent, reaction temperature, dehydration rate, and the like) as described below.

In the Examples in Patent Document 5, the ratio of the amount of water produced by the actual reaction is calculated by setting the amount of water produced in a case where the dehydration reaction proceeds 100% for all of the pentaerythritol and mercaptocarboxylic acid used in the synthesis as the theoretical amount of produced water and the calculation method differs from the theoretical amount of produced water illustrated in the present invention.

In the present embodiment, it is possible to obtain the thiol composition of the present invention by combining the above molar ratios and reaction conditions as appropriate; however, for example, reacting pentaerythritol with mercaptocarboxylic acid while continuously removing the water by-product from the system after the molar ratio of mercaptocarboxylic acid with respect to pentaerythritol is set to the above range is more preferable. Due to this, it is possible to more easily adjust the amount of the compound (B) with respect to the compound (A).

[Polymerizable Composition for Optical Material]

The polymerizable composition for an optical material of the present embodiment includes the thiol-containing composition for an optical material described above and a polyiso(thio)cyanate compound.

(Polyiso(thio)cyanate Compound)

As the polyiso(thio)cyanate compound, it is possible to use compounds known in the related art with no particular limitation as long as it is possible to exhibit the effect of the present invention, for example, it is possible to use the compounds disclosed in International Publication No. 2018/070383.

As a polyiso(thio)cyanate compound, a polyisocyanate compound is preferable, and it is preferable to include at least one selected from 2,5-bis(isocyanatomethyl)bicyclo-[2.2.1]-heptane, 2,6-bis(isocyanatomethyl)bicyclo-[2.2.1]-heptane, xylylene diisocyanate, bis (isocyanatocyclohexyl) methane, bis(isocyanatomethyl)cyclohexane, isophorone diisocyanate, hexamethylene diisocyanate, pentamethylene diisocyanate, tolylene diisocyanate, phenylene diisocyanate, and diphenylmethane diisocyanate.

The concentration of hydrolyzable chlorine (HC) in the polyisocyanate compound is 5 ppm or more, preferably 10 ppm or more, and more preferably 20 ppm or more, and 1000 ppm or less, preferably 500 ppm or less, and more preferably 200 ppm or less. The concentration of hydrolyzable chlorine (HC) is measured in accordance with the method for determining hydrolyzable chlorine described in JIS K-1603-3 (2007).

In a case where xylylene diisocyanate is used as a polyiso(thio)cyanate compound, the content ratio of chloromethylbenzyl isocyanate included in the xylylene diisocyanate is, with respect to the total weight of xylylene diisocyanate, for example, 0.2 ppm or more, preferably 6 ppm or more, more preferably 100 ppm or more, for example, 5000 ppm or less, preferably 4000 ppm or less, more preferably 3000 ppm or less, yet more preferably 1600 ppm or less, and particularly preferably 1000 ppm or less.

The content ratio of dichloromethylbenzyl isocyanate included in the xylylene diisocyanate is 0.6 ppm or more, and 60 ppm or less, preferably 10 ppm or less, and more preferably 5 ppm or less, with respect to the total weight of xylylene diisocyanate.

The concentration of hydrolyzable chlorine (HC) in xylylene diisocyanate is, for example, 10 ppm or more, preferably 20 ppm or more, and more preferably 30 ppm or more, for example, 1000 ppm or less, preferably 500 ppm or less, and more preferably 200 ppm or less. The concentration of hydrolyzable chlorine (HC) is measured in accordance with the method for determining hydrolyzable chlorine described in JIS K-1603-3 (2007).

As the polyiso(thio)cyanate compound, in a case where 2,5-bis(isocyanatomethyl)bicyclo-[2.2.1]-heptane and 2,6-bis(isocyanatomethyl)bicyclo-[2.2.1]-heptane is used, the concentration of hydrolyzable chlorine (HC) is, for example, 10 ppm or more, preferably 20 ppm or more, and more preferably 30 ppm or more, for example, 500 ppm or less, preferably 100 ppm or less, and more preferably 50 ppm or less. The concentration of hydrolyzable chlorine (HC) is measured in accordance with the method for determining hydrolyzable chlorine described in JIS K-1603-3 (2007).

The ratio (C1/P1) of a concentration C1 of hydrolyzable chlorine (HC) in polyisocyanate compounds and a peak area ratio P1 of the compound (b2-1) is preferably 500 or less, more preferably 170 or less, and particularly preferably 40 or less, with respect to the peak area 100 of the compound (A).

The ratio (C1/P2) of the concentration C1 of hydrolyzable chlorine (HC) in polyisocyanate compounds and a peak area ratio P2 of the compound (b3-1) is preferably 33 or less, more preferably 16 or less, and particularly preferably 6 or less, with respect to the peak area 100 of the compound (A).

The ratio (C2/P1) of the content ratio C2 of chloromethylbenzyl isocyanate included in xylylenediisocyanate and the peak area ratio P1 of the compound (b2-1) is preferably 2000 or less, more preferably 540 or less, and particularly preferably 200 or less, with respect to the peak area 100 of the compound (A).

The ratio (C2/P2) of the content ratio C2 of chloromethylbenzyl isocyanate included in xylylenediisocyanate and the peak area ratio P2 of the compound (b3-1) is preferably 140 or less, more preferably 50 or less, and particularly preferably 30 or less, with respect to the peak area 100 of the compound (A).

The ratio (C3/P1) of the content ratio C3 of dichloromethylbenzyl isocyanate included in xylylenediisocyanate and the peak area ratio P1 of the compound (b2-1) is preferably 30 or less, more preferably 3 or less, and particularly preferably 1 or less, with respect to the peak area 100 of the compound (A).

The ratio (C3/P2) of the content ratio C3 of dichloromethylbenzyl isocyanate included in xylylenediisocyanate and the peak area ratio P2 of the compound (b3-1) is preferably 2.00 or less, more preferably 0.35 or less, and particularly preferably 0.15 or less, with respect to the peak area 100 of the compound (A).

(Other Components)

It is possible for the polymerizable composition for an optical material of the present embodiment to include active hydrogen compounds such as polythiol compounds and polyol compounds other than compounds (A) and (B).

As the polythiol compounds other than the compounds (A) and (B), it is possible to select and use compounds known in the related art as long as it is possible to obtain the effects of the present invention, for example, it is possible to use the compounds disclosed in International Publication No. 2008/105138.

Specific examples of polythiol compounds include bis(mercaptoethyl)sulfide,
4-mercaptomethyl-1,8-dimercapto-3,6-dithiaoctane,
5,7-dimercaptomethyl-1,11-dimercapto-3,6,9-trithioundecane,
4,7-dimercaptomethyl-1,11-dimercapto-3,6,9-trithioundecane,
4,8-dimercaptomethyl-1,11-dimercapto-3,6,9-trithioundecane,
2,5-dimercaptomethyl-1,4-dithiane,
1,1,3,3-tetrakis (mercaptomethylthio) propane,
4,6-bis (mercaptomethylthio)-1,3-dithiane,
2-(2,2-bis (mercaptomethylthio) ethyl)-1,3-dithiethane, ethylene glycol bis(3-mercaptopropionate), and the like. It is possible to use at least one selected from the above.

As the polyol compound, it is possible to select and use compounds known in the related art as long as it is possible to obtain the effect of the present invention, for example, it is possible to use the compounds disclosed in International Publication No. 2017/047684. The polyol compound in the present embodiment is one or more aliphatic or alicyclic alcohols and specific examples thereof include linear or branched-chain aliphatic alcohols, alicyclic alcohols, and alcohols in which ethylene oxide, propylene oxide, or ε-caprolactone are added to the above alcohols, and the like.

The use ratio of the active hydrogen compound including compounds (A) and (B) and the polyiso (thio) cyanate compound is not particularly limited; however, usually, the molar ratio of SH groups and/or OH groups is in a range of 0.5 to 3.0, preferably 0.6 to 2.0, and even more preferably 0.8 to 1.3, with respect to NCO groups.

In the polymerizable composition for an optical material of the present embodiment, combinations (1) to (6) of a thiol-containing composition including the compound (A) below, the isocyanate monomer below, and other thiol compounds other than the compound (A) added as necessary are preferable.

(1) Combination of a thiol-containing composition including pentaerythritol tetrakismercaptopropionate, and xylylene diisocyanate (2) Combination of thiol-containing composition including pentaerythritol tetrakismercaptopropionate, and 2,5-bis(isocyanatomethyl)bicyclo-[2.2.1]-heptane, 2,6-bis(isocyanatomethyl)bicyclo-[2.2.1]-heptane, and 4-mercaptomethyl-1,8-dimercapto-3,6-dithiaoctane (3) Combination of thiol-containing composition including pentaerythritol tetrakismercaptopropionate, 2,5-bis(isocyanatomethyl)bicyclo-[2.2.1]-heptane and 2,6-bis(isocyanatomethyl)bicyclo-[2.2.1]-heptane, 5,7-dimercaptomethyl-1,11-dimercapto-3,6,9-trithioundecane and 4,7-dimercaptomethyl-1,11-dimercapto-3,6,9-trithioundecane and 4,8-dimercaptomethyl-1,11-dimercapto-3,6,9-trithioundecane (4) Combination of a thiol-containing composition including pentaerythritol tetrakismercaptopropionate, tolylene diisocyanate, and hexamethylene diisocyanate or pentamethylene diisocyanate (5) Combination of thiol-containing composition including pentaerythritol tetrakismercaptopropionate, diphenylmethane diisocyanate, and hexamethylene diisocyanate or pentamethylene diisocyanate (6) Combination of a thiol-containing composition including pentaerythritol tetrakismercaptoacetate and bis(isocyanatomethyl)cyclohexane and 2,5-dimercaptomethyl-1,4-dithiane.

In the present embodiment, in addition to the compounds (A) and (B), the polyiso(thio)cyanate compound, and the above components, other components such as a polymerization catalyst, an internal release agent, a resin modifier, and the like may be further included.

Examples of the polymerization catalyst include a tertiary amine compound and inorganic acid salts or organic acid salts thereof, a metal compound, a quaternary ammonium salt, or an organic sulfonic acid.

It is possible to use acidic phosphate esters as internal release agents. Examples of acidic phosphate esters include phosphoric acid monoesters and phosphoric acid diesters and it is possible to use each alone or in a mixture of two or more kinds.

Examples of resin modifiers include episulfide compounds, alcohol compounds, amine compounds, epoxy compounds, organic acids and anhydrides thereof, olefin compounds including (meth)acrylate compounds or the like, and the like.

It is possible to obtain the polymerizable composition for an optical material of the present embodiment by mixing the components described above.

[Molded Article]

The method for producing a molded product of the present embodiment is not particularly limited, but examples of preferable production methods include cast polymerization. First, a polymerizable composition is injected to a space between molds held by a gasket, a tape, or the like. At this time, depending on the physical properties required for the plastic lens to be obtained, in many cases, it is preferable to carry out a defoaming treatment under reduced pressure, a filtration treatment under pressure, reduced pressure, or the like, and the like as necessary.

Since the polymerization conditions vary greatly depending on the composition of the polymerizable composition, the kind and amount of the catalyst used, the shape of the mold, and the like, the conditions are not limited, but the above are performed for approximately 1 to 50 hours at a temperature of −50° C. to 150° C. In some cases, it is preferable to carry out the curing while holding or gradually raising the temperature in a temperature range of 10° C. to 150° C. for 1 to 48 hours.

The resin molded product may be subjected to a treatment such as annealing as necessary. The treatment temperature is usually 50° C. to 150° C., but preferably 90° C. to 140° C., and more preferably 100° C. to 130° C.

In the present embodiment, when forming the resin, in addition to the "other components" described above, in the same manner as known molding methods, various additives such as a chain extender, a cross-linking agent, a radical scavenger, a light stabilizer, an ultraviolet stabilizer, an antioxidant, a bluing agent, an oil soluble dye, a filler, an adhesion improver, an antibacterial agent, an antistatic agent, and the like may be added in accordance with the purpose.

[Use]

It is possible to obtain the resin obtained from the polymerizable composition for an optical material of the present embodiment as molded products of various shapes by changing the kind of mold at the time of cast polymerization.

For the molded product obtained from the polymerizable composition for an optical material of the present embodiment, use is possible in various optical materials such as plastic lenses since it is possible to obtain a material which combines excellent surface hardness without loss of transparency. In particular, it is possible to suitably use the molded product as a plastic spectacle lens or a plastic polarized lens.

The plastic lens of the present embodiment may be provided with a coating layer described below on a surface thereof.

The plastic lens of the present embodiment preferably uses a molded product obtained by curing the polymerizable compositions for an optical material (1) to (6) described above.

The plastic lens obtained from the polymerizable composition for an optical material (1) has a thioester group molar number with respect to the entire plastic lens of 0.0007 mmol/g to 0.146 mmol/g, preferably 0.007 mmol/g to 0.110 mmol/g, as measured by the following method.

The plastic lenses obtained from the polymerizable compositions for an optical material (2), (3), or (6) have a thioester group molar number with respect to the entire plastic lens of 0.0003 mmol/g to 0.062 mmol/g, preferably 0.003 mmol/g to 0.047 mmol/g, as measured by the following method.

(Measurement Method)

Residual functional group analysis by IR measurement

The IR spectrum of a sample (molded product) cut to a thickness of 0.30 mm and subjected to a polishing process was measured using a Spectrum One IR analyzer produced by PERKIN-ELMER Inc. The thioester group (—C(O)S—) molar number was determined by calculation by determining the absorbance by the baseline method using the absorption at $1720 \text{ cm}^{-1}$.

[Plastic Spectacle Lens]

The plastic spectacle lens using the lens base material composed of the molded product of the present embodiment may be used after application of a coating layer on one surface or both surfaces thereof as necessary.

The plastic spectacle lens of the present embodiment is composed of a lens base material composed of the polymerizable composition described above and a coating layer.

Specific examples of the coating layer include a primer layer, a hard coat layer, an anti-reflection layer, an anti-fog coating layer, an anti-fouling layer, a water repellent layer, and the like. It is also possible to use each of these coating layers alone, or to use a plurality of coating layers in multiple layers. In a case of applying coating layers on both surfaces, the same coating layer may be applied to each surface or different coating layers may be applied to each surface.

In each of these coating layers, an infrared absorber for the purpose of protecting eyes from infrared rays, a light stabilizer, an antioxidant, and a photochromic compound for the purpose of improving the weather resistance of the lens, a dye or a pigment for the purpose of improving the fashionability of the lens, an antistatic agent, and other known additives for improving the performance of the lens may be used in combination.

Various leveling agents for the purpose of improving applicability may be used for layers to be coated by coating.

In addition, an anti-fogging layer, an anti-pollution layer, or a water repellent layer may be formed over the anti-reflection layer as necessary.

[Plastic Polarized Lens]

The plastic polarized lens of the present embodiment includes a polarizing film, and a base material layer formed on at least one surface of the polarizing film and composed of the molded product obtained by curing the polymerizable composition for an optical material of the present embodiment.

It is possible to form the polarizing film in the present embodiment of a thermoplastic resin. Examples of thermoplastic resins include thermoplastic polyester, thermoplastic polycarbonate, thermoplastic polyolefin, thermoplastic polyimide, and the like. From the viewpoints of water resistance, heat resistance, and molding processability, thermoplastic polyester and thermoplastic polycarbonate are preferable, and thermoplastic polyester is more preferable.

Specific examples of polarizing films include a thermoplastic polyester polarizing film containing a dichroic dye, a polyvinyl alcohol polarizing film containing iodine, a polyvinyl alcohol polarizing film containing a dichroic dye, and the like.

It is possible to obtain the plastic polarized lens of the present embodiment by providing, on at least one surface of such a polarizing film, a base material layer obtained by curing the polymerizable composition for an optical material of the present embodiment.

The method for producing a plastic polarized lens is not particularly limited, but preferable examples thereof include a cast polymerization method.

The coating layer similar to that of the plastic spectacle lens may be formed on the surface of the obtained base material layer.

Embodiments of the present invention were described above, but these are examples of the present invention and it is possible to adopt various configurations other than those described above in a range in which the effects of the present invention are not impaired.

EXAMPLES

A detailed description will be given below of the present invention with reference to Examples, but the present invention is not limited by these Examples. In the Examples and Comparative Examples, the methods used for evaluation and the apparatuses used are as follows.

Composition ratio analysis (composition ratio of the compound (A) and compound (B) included in the thiol-containing composition for an optical material)

HPLC model: SPD-10A produced by Shimadzu Corporation

Detector: RI detector

Column: YMC column ODS-A-312 (150 mm×6 mm. I.D.) 5 μm

Temperature condition: 40° C.

Mobile phase: Water/acetonitrile (35/65) aqueous solution

Flow rate: 1.0 ml/min

Analysis sample preparation: Mix and dissolve 3 g of sample with 3 g of acetonitrile Injection volume: 1 μL Calculation of composition ratio: The peak area of each compound was calculated with respect to the peak area 100 of the pentaerythritol tetrakis 3-mercaptopropionic acid ester.

(Refractive Index (Ne), Abbe Number (Ve))

Measurement was carried out at 20° C. using a Pullfrich refractometer.

(YI)

A resin plate having a thickness of 9 mm was prepared and the yellowness (YI) was measured on a color Chroma Meter (produced by Konica Minolta Inc., CR-200).

(Distortion)

The distortions of the 10 prepared lenses were measured with a distortion tester SVP-10 (produced by Toshiba Corporation) and evaluated according to the following criteria.

A: no distortion was observed in 9 to 10 lenses.
B: no distortion was observed in 7 to 8 lenses.
C: no distortion was observed in 5 to 6 lenses.
X: no distortion was observed in 4 or fewer lenses.

(Striae)

Each of ten prepared lenses was irradiated with a high-pressure mercury lamp and the projected images were visually observed and evaluated according to the following criteria.

A: no striae were observed in 9 to 10 lenses.
B: no striae were observed in 7 to 8 lenses.
C: no striae were observed in 5 to 6 lenses.
X: no striae were observed in 4 or fewer lenses.

(Cloudiness)

The prepared lenses were exposed to a projector in a dark room and the cloudiness of the lenses was visually observed and evaluated according to the following criteria.

A: no cloudiness was observed in 9 to 10 lenses.
B: no cloudiness was observed in 7 to 8 lenses.
C: no cloudiness was observed in 5 to 6 lenses.
X: no cloudiness was observed in 4 or fewer lenses.

(Dyeability Test)

Using Dianix Brown S-3R produced by Dystar as a dyeing agent, 50 ppm thereof was dissolved in pure water to adjust a dye dispersion solution. After heating the result to 90° C., resin samples (10 pieces) with a thickness of 9 mm were immersed therein for 60 minutes at 90° C. and dyed. After dyeing, the sample pieces were scanned using a UV spectrometer (produced by Shimadzu Corporation, UV-1600) from a wavelength of 400 to 800 nm and the transmittance (% T) was measured at 460 nm, which was the maximum absorption wavelength. The average value of the transmittance of 10 lenses was calculated and evaluated based on the following criteria.

B: The transmittance blur width is less than ±5% of the average value of the transmittances of the 10 lenses C: The transmittance blur width is less than ±6% to ±10% of the average value of the transmittances of the 10 lenses X: The transmittance blur width is ±10% or more of the average value of the transmittances of the 10 lenses (Heat Resistance (Glass Transition Temperature: Tg))

Measurement was carried out by the TMA penetration method (50 g load, 0.5 mmφ pin tip, temperature increase rate of 10° C./min) in a TMA-60 thermo-mechanical analyzer produced by Shimadzu Corporation.

(Ball Drop Test)

With respect to lenses with a center thickness of 0.3 mm, diameter of 75 mm, and S=−4.75D shape, 11 kinds of iron balls of different weights of 8 g, 16 g, 28 g, 33 g, 45 g, 67 g, 95 g, 112 g, 174 g, 226 g, and 534 g were dropped in order from light to heavy from a position at a height of 127 cm (50 inches) onto the center portion of the lens and the lenses were tested for damage. Ten lenses were tested, the maximum value of the weight of the iron balls that did not cause damage was confirmed for each lens, and the average value of the maximum values for the ten lenses was determined as the "average value of the weight that did not cause damage". The impact resistance was evaluated according to this average value.

Example 1

(Synthesis of Pentaerythritol 3-Mercaptopropionic Acid Ester (Preparation of Thiol Composition))

Into a four-necked reaction flask equipped with a stirrer, a Dean-Stark tube, a nitrogen gas purge tube, and a thermometer, 136.9 parts by weight of pentaerythritol of 99.5% purity, 406.3 parts by weight of 3-mercaptopropionic acid, 3.8 parts by weight of p-toluenesulfonic acid monohydrate, and 185.2 parts by weight of toluene were added. The molar ratio of 3-mercaptopropionic acid with respect to pentaerythritol was 3.80. 120 minutes after starting to increase the temperature using an oil bath, reflux was started when the internal temperature reached 97° C. (the oil bath temperature was 113° C.). After starting the reflux, a reaction was carried out for 7 hours (internal temperature: 97° C. to 121° C.). During this time, the water by-product was continuously extracted from the system under reflux. The amount of water extracted from the system was 93.2% of the theoretical amount of produced water. After cooling, the reaction solution was washed with a base, then washed with water, and toluene and a small amount of water were removed under heating and reduced pressure. Thereafter, filtering was carried out to obtain 462.3 parts by weight of the thiol composition. The obtained thiol composition was subjected to composition ratio analysis using HPLC. The peak area ratio of each compound with respect to the peak area 100 of compound (A1) was as follows.

Compound (A1) (all n in General Formula (a) are 2): 100% (retention time: 7.8 to 8.8)

Compound (B2-1) (all n in General Formula (b2-1) are 2): 1.4% (retention time: 3.3 to 4.3)

Compound (B3-1) (all n in General Formula (b3-1) are 2): 26.4% (retention time: 4.6 to 5.6)

Compound (B3-2) (all n in General Formula (b3-2) are 2): 1.5% (retention time: 5.7 to 6.7)

Compound (B4-2) (all n in General Formula (b4-2) are 2): 6.9% (retention time: 10.2 to 11.2)

(Production of Plastic Lenses)

50.6 parts by weight of a mixture of 2,5-bis(isocyanatomethyl)-bicyclo[2.2.1]heptane and 2,6-bis(isocyanatomethyl)-bicyclo[2.2.1]heptane, 0.06 parts by weight of dibutyltin dichloride as a curing catalyst, 0.12 parts by weight of acidic phosphate ester (produced by Stepan Corporation, product name: Zelec UN), and 0.05 parts by weight of 2-(3,5-di-t-butyl-2-hydroxyphenyl)-5-chlorobenzotriazole (produced by Ciba Specialty Chemicals, product name:

Tinuvin 327) as an ultraviolet absorber were mixed and dissolved at 15° C. to 20° C. 25.5 parts by weight of a polythiol in which the main component was 1,2-bis[(2-mercaptoethyl)thio]-3-mercaptopropane and 23.9 parts by weight of the obtained thiol composition were charged therein and mixed to form a mixed and uniform solution. The uniform solution was defoamed at 600 Pa for 1 hour, filtered through a 1 μm PTFE filter, and then injected into a mold having diameter of 75 mm and a thickness of 9 mm formed of a glass mold and tape to prepare lenses. The mold was placed in an oven and the temperature was gradually increased from 20° C. to 120° C. for 20 hours to carry out polymerization. After the polymerization was completed, the mold was removed from the oven and released to obtain the lenses. The obtained lenses were further annealed at 130° C. for 4 hours. The results of viscosity measurement of the polymerizable compositions and lenses below are shown in Table-1.

The thioester group molar number of the lenses measured by the following method satisfied the following numerical range.

0.0003 mmol/g to 0.062 mmol/g (Method)

The IR spectrum of a sample (molded product) cut to a thickness of 0.30 mm and subjected to a polishing process was measured using a Spectrum One IR analyzer produced by PERKIN-ELMER. The thioester group (—C(O)S—) molar number was determined by calculation by determining the absorbance by the baseline method using the absorption at 1720 cm$^{-1}$.

(Viscosity of Polymerizable Composition After 7 Hours at 20° C.)

50.6 parts by weight of a mixture of 2,5-bis(isocyanatomethyl)-bicyclo[2.2.1]heptane and 2,6-bis(isocyanatomethyl)-bicyclo[2.2.1]heptane, 0.06 parts by weight of dibutyltin dichloride as a curing catalyst, 0.12 parts by weight of Zelec UN produced by Stepan (trade name, acidic phosphate ester), 0.05 parts by weight of Tinuvin 327 produced by Ciba Specialty Chemicals (trade name, ultraviolet absorber) 2-(3,5-di-t-butyl-2-hydroxyphenyl)-5-chlorobenzotriazole were mixed and dissolved at 20° C. 25.6 parts by weight of polythiol in which the main component was 1,2-bis[(2-mercaptoethyl)thio]-3-mercaptopropane, and 23.9 parts by weight of the obtained thiol-containing composition were charged therein and mixed to form a mixed and uniform solution. The mixed and uniform solution preparation time was set as 0 hours and the viscosity after 7 hours at 20° C. was measured with a B-type viscometer and evaluated according to the following criteria.

B: 90 cps or less

X: More than 90 cps

Examples 2 to 12 and Comparative Examples 1 to 3

The synthesis of pentaerythritol 3-mercaptopropionic acid ester (preparation of thiol composition) was performed in the same manner as in Example 1, except that the molar ratio of pentaerythritol and 3-mercaptopropionic acid, the reaction time after the start of reflux, and the dehydration rate were changed as shown in Table-1 and the polymerizable compositions and plastic lenses were prepared.

The composition ratio analysis results of the obtained thiol compositions, the viscosity measurement results of the polymerizable composition after 7 hours at 20° C., and the measurement results of the plastic lenses are shown in Table-1.

TABLE 1

|  | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|
| MPA/PN (molar ratio) | 3.80 | 3.85 | 3.90 | 3.93 | 4.00 | 4.00 | 4.10 | 4.15 | 4.50 | 5.00 | 4.00 | 4.15 |
| Reaction time (h) after reflux start | 7 | 7 | 7 | 7 | 11 | 7 | 7 | 7 | 7 | 7 | 7 | 7 |
| Compound (b2-1) | 1.4 | 1.4 | 0.8 | 1.1 | 0.5 | 0.7 | 0.7 | 0.1 | 0.0 | 0.0 | 0.4 | 0.7 |
| Compound (b3-1) | 26.4 | 26.7 | 20.1 | 23.4 | 15.6 | 18.2 | 18.1 | 9.1 | 3.6 | 3.6 | 16.9 | 18.1 |
| Compound (b3-2) | 1.5 | 1.6 | 1.4 | 1.4 | 1.1 | 1.8 | 1.3 | 0.9 | 0.4 | 0.4 | 3.2 | 4.4 |
| Compound (b4-2) | 6.9 | 7.1 | 8.5 | 7.3 | 8.4 | 11.1 | 8.4 | 16.4 | 12.5 | 12.5 | 22.2 | 21.0 |
| Total amount of compound (B) | 36.2 | 36.8 | 30.8 | 33.2 | 25.6 | 31.8 | 28.5 | 26.5 | 16.5 | 16.5 | 42.7 | 44.2 |
| Dehydration rate | 93.2 | 95.2 | 93.1 | 93.2 | 96.3 | 93.8 | 95.7 | 96.8 | 99.7 | 99.8 | 99.3 | 99.3 |
| Refraction index (ne) | 1.598 | 1.598 | 1.598 | 1.597 | 1.598 | 1.598 | 1.598 | 1.598 | 1.598 | 1.598 | 1.598 | 1.598 |
| Abbe No. (ve) | 39 | 39 | 39 | 39 | 39 | 39 | 39 | 39 | 39 | 39 | 39 | 39 |
| YI | 3.3 | 3.2 | 3.2 | 3.2 | 3.2 | 3.3 | 3.2 | 3.3 | 3.3 | 3.3 | 3.5 | 3.5 |
| Distortion | A | A | A | A | A | A | A | A | A | A | A | A |
| Striae | A | A | A | A | A | A | A | A | A | A | C | C |
| Cloudiness | A | A | A | A | A | A | A | A | A | A | A | A |
| Viscosity of polymerizable composition after 7 hours at 20° C. | B | B | B | B | B | B | B | B | B | B | B | B |
| Dyeability | B | B | B | B | B | B | B | B | B | B | B | B |
| Heat resistance (° C.) | 112 | 112 | 111 | 111 | 110 | 111 | 110 | 110 | 110 | 111 | 112 | 111 |
| Ball drop test | 38 | 37 | 38 | 37 | 39 | 38 | 37 | 38 | 37 | 37 | 37 | 37 |

|  | Comparative Example 1 | Comparative Example 2 | Comparative Example 3 |
|---|---|---|---|
| MPA/PN (molar ratio) | 3.00 | 3.50 | 5.00 |
| Reaction time (h) after reflux start | 7 | 7 | 10 |

TABLE 1-continued

| | | | |
|---|---|---|---|
| Compound (b2-1) | 38.1 | 6.4 | 0.0 |
| Compound (b3-1) | 155.5 | 56.3 | 4.5 |
| Compound (b3-2) | 5.0 | 2.6 | 1.0 |
| Compound (b4-2) | 3.9 | 5.3 | 197.4 |
| Total amount of compound (B) | 202.5 | 70.6 | 202.9 |
| Dehydration rate | 73.2 | 85.1 | 124.3 |
| Refraction index (ne) | 1.596 | 1.597 | 1.597 |
| Abbe No. (ve) | 40 | 39 | 39 |
| YI | 4.1 | 3.4 | 3.3 |
| Distortion | A | A | A |
| Striae | X | X | C |
| Cloudiness | A | A | A |
| Viscosity of polymerizable composition after 7 hours at 20° C. | X | X | X |
| Dyeability | X | C | B |
| Heat resistance (° C.) | 115 | 116 | 112 |
| Ball drop test | 34 | 33 | 37 |

This application claims priority based on Japanese Application No. 2019-085312 filed on Apr. 26, 2019, the entire disclosure of which is incorporated herein.

The invention claimed is:

1. A thiol-containing composition for an optical material comprising: a compound (A) represented by General Formula (a)

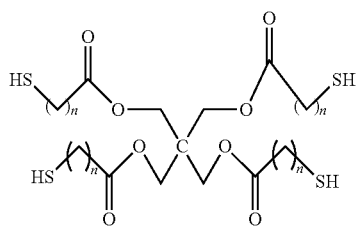

(a)

wherein, in General Formula (a), n is an integer of 1 to 3, and a plurality of present n's may be the same or different; and a compound (B) composed of one or two or more compounds selected from the group consisting of a compound (b2-1) represented by General Formula (b2-1), a compound (b3-1) represented by General Formula (b3-1), a compound (b3-2) represented by General Formula (b3-2), and a compound (b4-2) represented by General Formula (b4-2), wherein in high-performance liquid chromatography measurement, a total peak area ratio of the compound included in the compound (B) is 0.1% to 40.0%, and a total peak area ratio of the compound (b3-2) and the compound (b4-2) is 20.0% or less, with respect to a peak area 100 of the compound (A),

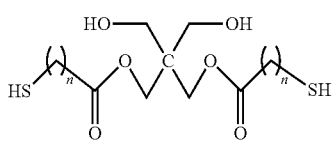

(b2-1)

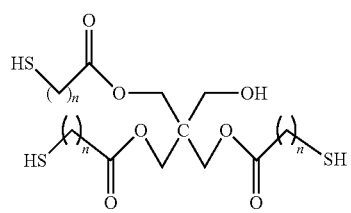

(b3-1)

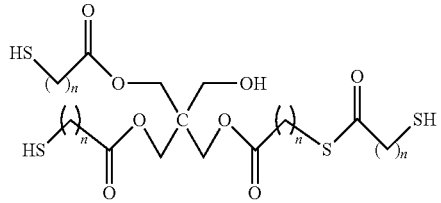

(b3-2)

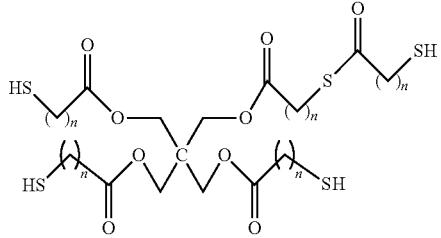

(b4-2)

wherein, in General Formula (b2-1), General Formula (b3-1), General Formula (b3-2), and General Formula (b4-2), n is an integer of 1 to 3, and in each General Formula, a plurality of present n's may be the same or different.

2. The thiol-containing composition for an optical material according to claim 1,
wherein, in high-performance liquid chromatography measurement, the total peak area ratio of the compound included in the compound (B) is 10.0% to 40.0% with respect to the peak area 100 of the compound (A).

3. The thiol-containing composition for an optical material according to claim 1, wherein, in high-performance liquid chromatography measurement, a peak area ratio of the compound (b2-1) is 5.0% or less with respect to the peak area 100 of the compound (A).

4. The thiol-containing composition for an optical material according to claim 1,
wherein, in high-performance liquid chromatography measurement, a peak area ratio of the compound (b3-2) is 5.0% or less with respect to the peak area 100 of the compound (A).

5. The thiol-containing composition for an optical material according to claim 1,
wherein, in high-performance liquid chromatography measurement, a peak area ratio of the compound (b4-2) is 20.0% or less with respect to the peak area 100 of the compound (A).

6. The thiol-containing composition for an optical material according to claim 1,
wherein the compound (A) is pentaerythritol tetrakismercaptopropionate, and
n in the General Formula in the compound (B) is 2.

7. The thiol-containing composition for an optical material according to claim 1,
wherein the compound (A) is pentaerythritol tetrakismercaptoacetate, and
n in the General Formula in the compound (B) is 1.

8. A polymerizable composition for an optical material comprising:
the thiol-containing composition for an optical material according to claim 1; and
a polyiso(thio)cyanate compound.

9. The polymerizable composition for an optical material according to claim 8,
wherein the polyiso(thio)cyanate compound includes at least one selected from 2,5-bis(isocyanatomethyl)bicyclo-[2.2.1]-heptane, 2,6-bis(isocyanatomethyl)bicyclo-[2.2.1]-heptane, xylylene diisocyanate, bis(isocyanatocyclohexyl)methane, bis(isocyanatomethyl)cyclohexane, isophorone diisocyanate, hexamethylene diisocyanate, pentamethylene diisocyanate, tolylene diisocyanate, diphenylmethane diisocyanate, and phenylene diisocyanate.

10. A molded product formed by curing the polymerizable composition for an optical material according to claim 8.

11. An optical material composed of the molded product according to claim 10.

12. A plastic lens composed of the molded product according to claim 10.

13. A thiol-containing composition for an optical material, comprising:
a compound (A) represented by General Formula (a)

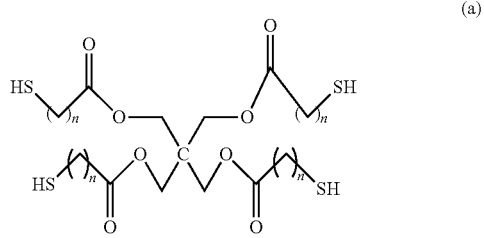

(a)

wherein, in General Formula (a), n is an integer of 1 to 3, and a plurality of present n's may be the same or different; and a compound (B) composed of a compound (b2-1) represented by General Formula (b2-1), a compound (b3-1) represented by General Formula (b3-1), a compound (b3-2) represented by General Formula (b3-2), and a compound (b4-2) represented by General Formula (b4-2),
wherein in high-performance liquid chromatography measurement, a total peak area ratio of the compounds included in the compound (B) is 0.1% to 40.0%, and a total peak area ratio of the compound (b3-2) and the compound (b4-2) is 20.0% or less, with respect to a peak area 100 of the compound (A),

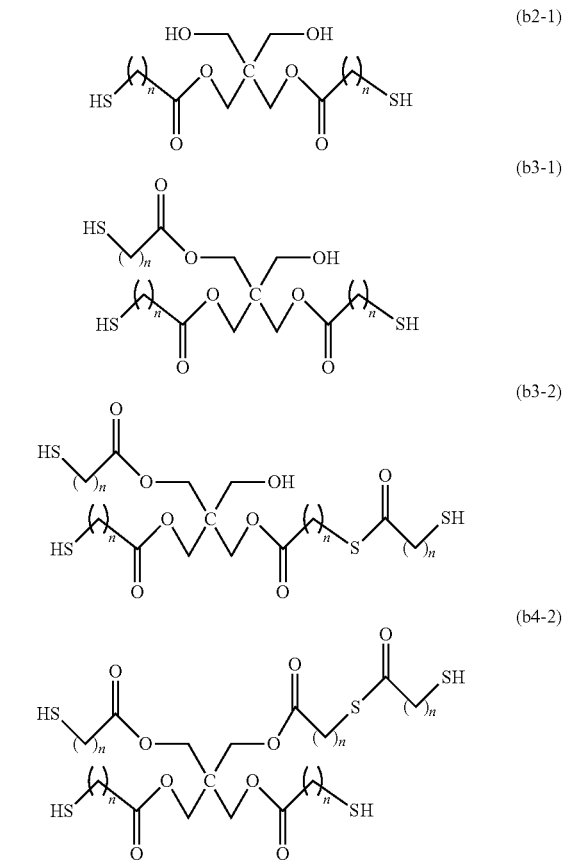

wherein, in General Formula (b2-1), General Formula (b3-1), General Formula (b3-2), and General Formula (b4-2), n is an integer of 1 to 3, and in each General Formula, a plurality of present n's may be the same or different.

14. A thiol-containing composition for an optical material, comprising:
a compound (A) represented by General Formula (a)

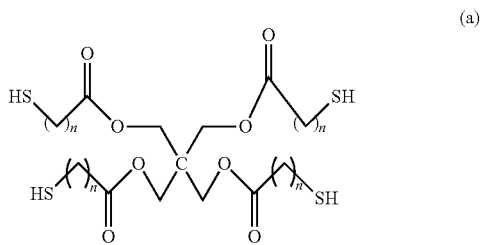

(a)

wherein, in General Formula (a), n is an integer of 1 to 3, and a plurality of present n's may be the same or different; and a compound (B) composed of one or two or more compounds selected from the group consisting of a compound (b2-1) represented by General Formula (b2-1), a compound (b3-1) represented by General Formula (b3-1), a compound (b3-2) represented by General Formula (b3-2), and a compound (b4-2) represented by General Formula (b4-2), wherein, in high-performance liquid chromatography measurement, a peak area ratio of the compound (b2-1) is 0.0%, a total peak area ratio of the compound included in the compound (B) is 0.1% to 40.0%, and a total peak area ratio of the compound (b3-2) and the compound (b4-2) is 20.0% or less, with respect to a peak area 100 of the compound (A),

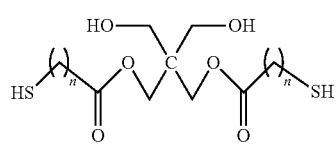
(b2-1)

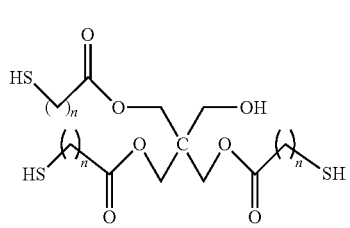
(b3-1)

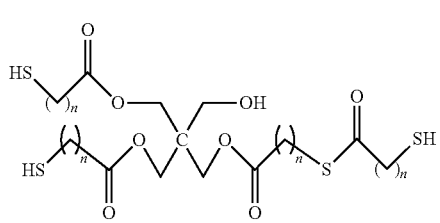
(b3-2)

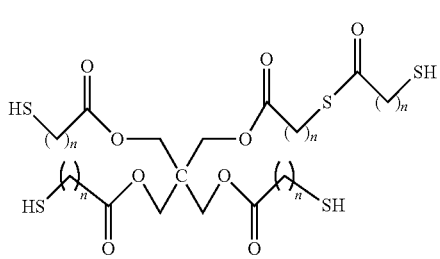
(b4-2)

wherein, in General Formula (b2-1), General Formula (b3-1), General Formula (b3-2), and General Formula (b4-2), n is an integer of 1 to 3, and in each General Formula, a plurality of present n's may be the same or different.

15. A thiol-containing composition for an optical material comprising:

a compound (A) represented by General Formula (a)

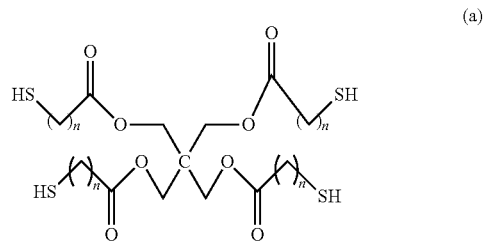
(a)

wherein, in General Formula (a), n is an integer of 1 to 3, and a plurality of present n's may be the same or different;

a compound (b3-2) represented by General Formula (b3-2); and a compound (b4-2) represented by General Formula (b4-2)

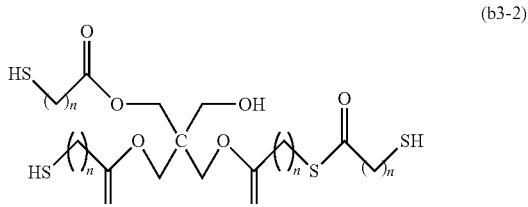
(b3-2)

wherein, in General Formula (b3-2), n is an integer of 1 to 3, and a plurality of present n's may be the same or different,

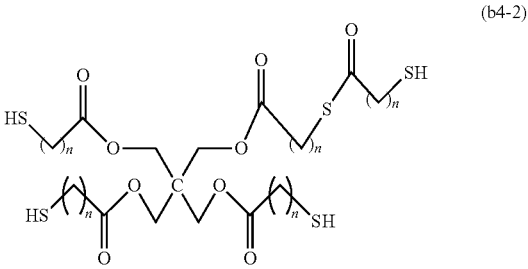
(b4-2)

wherein, in General Formula (b4-2), n is an integer of 1 to 3, and a plurality of present n's may be the same or different, wherein, in high-performance liquid chromatography measurement, a total peak area ratio of the compound (b3-2) and the compound (b4-2) is 20.0% or less with respect to a peak area 100 of the compound (A).

16. A thiol-containing composition for an optical material, comprising:

a compound (A) represented by General Formula (a)

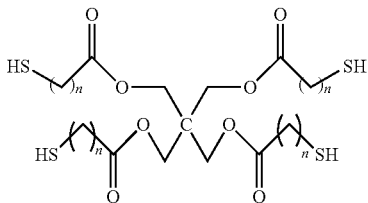

(a)

wherein, in General Formula (a), n is an integer of 1 to 3, and a plurality of present n's may be the same or different; and a compound (B) composed of a compound (b2-1) represented by General Formula (b2-1), a compound (b3-1) represented by General Formula (b3-1), a compound (b3-2) represented by General Formula (b3-2), and a compound (b4-2) represented by General Formula (b4-2), wherein in high-performance liquid chromatography measurement, a total peak area ratio of the compounds included in the compound (B) is 0.1% to 60.0%, and a total peak area ratio of the compound (b3-2) and the compound (b4-2) is 20.0% or less, with respect to a peak area 100 of the compound (A),

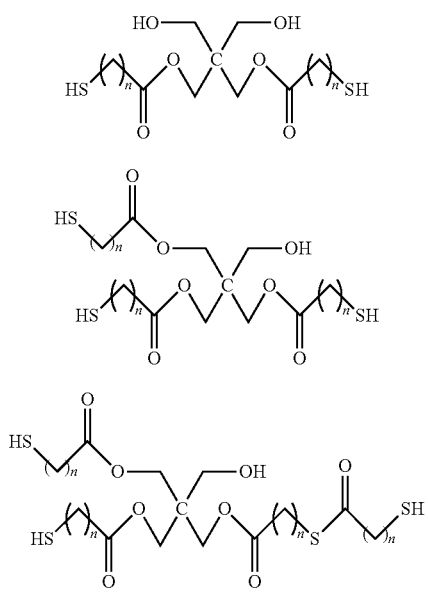

wherein, in General Formula (b2-1), General Formula (b3-1), General Formula (b3-2), and General Formula (b4-2), n is an integer of 1 to 3, and in each General Formula, a plurality of present n's may be the same or different.

17. A thiol-containing composition for an optical material, comprising:

a compound (A) represented by General Formula (a)

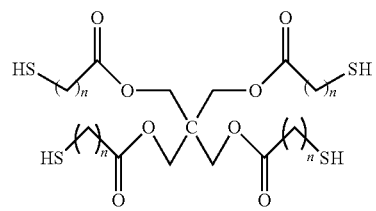

(a)

wherein, in General Formula (a), n is an integer of 1 to 3, and a plurality of present n's may be the same or different; and a compound (B) composed of one or two or more compounds selected from the group consisting of a compound (b2-1) represented by General Formula (b2-1), a compound (b3-1) represented by General Formula (b3-1), a compound (b3-2) represented by General Formula (b3-2), and a compound (b4-2) represented by General Formula (b4-2), wherein, in high-performance liquid chromatography measurement, a peak area ratio of the compound (b2-1) is 0.0%, a total peak area ratio of the compound included in the compound (B) is 0.1% to 60.0%, and a total peak area ratio of the compound (b3-2) and the compound (b4-2) is 20.0% or less, with respect to a peak area 100 of the compound (A),

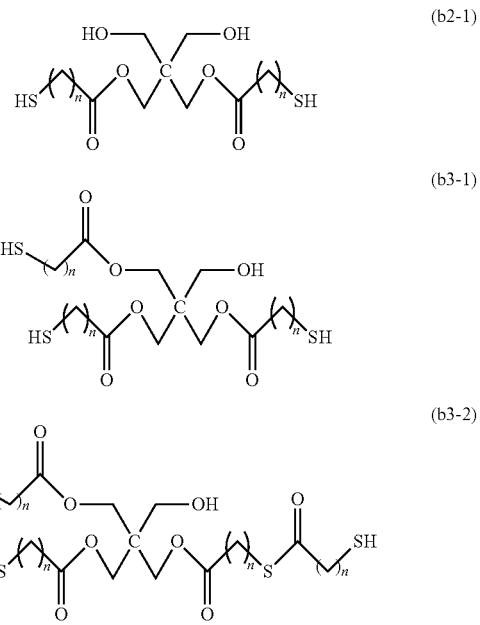

-continued (b4-2)

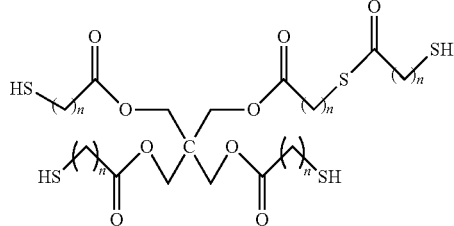

wherein, in General Formula (b2-1), General Formula (b3-1), General Formula (b3-2), and General Formula (b4-2), n is an integer of 1 to 3, and in each General Formula, a plurality of present n's may be the same or different.

18. A plastic lens composed of a molded product formed by curing a polymerizable composition for an optical material,
wherein a thioester group molar number is 0.0003 mmol/g to 0.146 mmol/g,
the polymerizable composition for an optical material comprising:
a thiol-containing composition for an optical material; and
a polyiso(thio)cyanate compound,
wherein the thiol-containing composition for an optical material comprises: a compound (A) represented by General Formula (a)

(a)

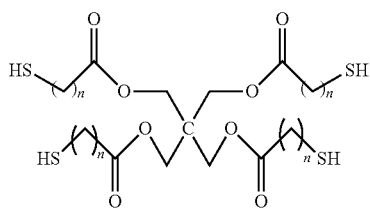

wherein, in General Formula (a), n is an integer of 1 to 3, and a plurality of present n's may be the same or different; and
a compound (B) composed of one or two or more compounds selected from the group consisting of a compound (b2-1) represented by General Formula (b2-1), a compound (b3-1) represented by General Formula (b3-1), a compound (b3-2) represented by General Formula (b3-2), and a compound (b4-2) represented by General Formula (b4-2), wherein in high-performance liquid chromatography measurement, a total peak area ratio of the compound included in the compound (B) is 0.1% to 60.0% with respect to a peak area 100 of the compound (A), (b2-1)

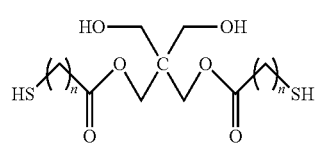

(b3-1)

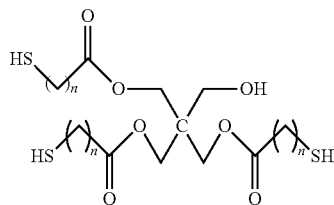

(b3-2)

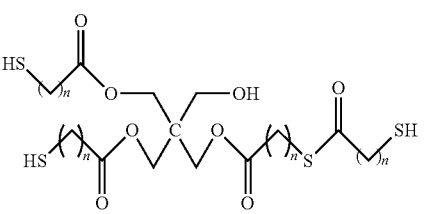

(b4-2)

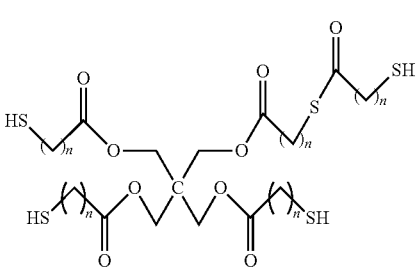

wherein, in General Formula (b2-1), General Formula (b3-1), General Formula (b3-2), and General Formula (b4-2), n is an integer of 1 to 3, and in each General Formula, a plurality of present n's may be the same or different.

* * * * *